US011465906B2

(12) United States Patent
Choi et al.

(10) Patent No.: US 11,465,906 B2
(45) Date of Patent: Oct. 11, 2022

(54) METHOD FOR PURIFYING WASTE SOLVENT

(71) Applicant: LG CHEM, LTD., Seoul (KR)

(72) Inventors: Seung Won Choi, Daejeon (KR); Sung Keun Jang, Daejeon (KR); Eun Jung Joo, Daejeon (KR); Young Ho Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 417 days.

(21) Appl. No.: 16/496,061

(22) PCT Filed: Nov. 12, 2018

(86) PCT No.: PCT/KR2018/013736
§ 371 (c)(1),
(2) Date: Sep. 20, 2019

(87) PCT Pub. No.: WO2019/093847
PCT Pub. Date: May 16, 2019

(65) Prior Publication Data
US 2020/0115244 A1    Apr. 16, 2020

(30) Foreign Application Priority Data

Nov. 13, 2017 (KR) .................... 10-2017-0150507
Sep. 20, 2018 (KR) .................... 10-2018-0113172

(51) Int. Cl.
*B01D 3/14* (2006.01)
*C01B 33/158* (2006.01)
*C07C 29/80* (2006.01)
*B01D 3/42* (2006.01)

(52) U.S. Cl.
CPC .......... *C01B 33/1585* (2013.01); *B01D 3/143* (2013.01); *B01D 3/4205* (2013.01); *C07C 29/80* (2013.01)

(58) Field of Classification Search
CPC ..... C01B 33/1585; C07C 29/80; B01D 3/143; B01D 3/4205
See application file for complete search history.

(56) References Cited

U.S. PATENT DOCUMENTS

| 4,349,415 | A | * | 9/1982 | DeFilippi | B01D 3/343 |
| | | | | | 203/16 |
| 4,399,000 | A | * | 8/1983 | Tedder | C07C 29/86 |
| | | | | | 568/918 |
| 5,217,579 | A | * | 6/1993 | Kusakabe | C02F 1/048 |
| | | | | | 159/DIG. 10 |
| 7,915,452 | B2 | * | 3/2011 | Amakawa | C07C 211/27 |
| | | | | | 564/385 |
| 10,414,894 | B2 | * | 9/2019 | Bertino | C08J 9/286 |
| 2009/0192334 | A1 | * | 7/2009 | Amakawa | C07C 209/48 |
| | | | | | 564/385 |
| 2017/0218160 | A1 | * | 8/2017 | Bertino | C08J 9/28 |
| 2018/0370809 | A1 | * | 12/2018 | Lee | B01D 5/0045 |
| 2019/0344333 | A1 | * | 11/2019 | Golfetto | C08J 9/22 |
| 2020/0407231 | A1 | * | 12/2020 | Choi | B01J 13/0091 |

FOREIGN PATENT DOCUMENTS

| CN | 104760964 | 7/2015 |
| CN | 105031960 | 11/2015 |
| CN | 205145937 U | 4/2016 |
| JP | H06-191822 | 7/1994 |
| JP | H11-28353 | 2/1999 |
| JP | H11-335115 | 12/1999 |
| JP | 2005-334871 | 12/2005 |
| KR | 10-2017-0110994 | 10/2017 |

OTHER PUBLICATIONS

CN 105031960, Liang et al Nov. 2015, see maching translation in English.*
Espacenet Machine Translation of Cn 105031960A Obtained Mar. 17, 2022. (Year: 2022).*
Espacenet Machine Translation of CN104760964A Obtained Mar. 17, 2022. (Year: 2022).*
Chemical Society of Japan, fifth edition, Experimental Chemistry Course, Basics I: Basics of experiments and information, 2013, vol. 1, pp. 167 to pp. 189.
Yang et al., Principles of Food Engineering, China Agriculture Press, 2001, pp. 348-355.
"Functional Materials 2 Low-Dimensional Materials," Chinese Materials Research Society, Beijing Chemical Industry Press, 1997, pp. 239-243.
Zhang, M., "Nano and New Materials Album 4," Material Reports, 2005, pp. 32-34.
Chen, Z., "Inorganic Nonmetallic Materials Science 2nd Edition," Northwestern Polytechnical University Press, 2016, pp. 302-304.

* cited by examiner

*Primary Examiner* — Jonathan Miller
(74) *Attorney, Agent, or Firm* — Dentons US LLP

(57) ABSTRACT

Provided is a method for purifying a waste solvent by removing carbon dioxide contained in a waste solvent derived from supercritical waste liquid generated after supercritical drying by a decompression process, and removing ammonia by a multi-stage distillation process to obtain a solvent of high purity, which can be reused in producing silica aerogel or a silica aerogel blanket.

11 Claims, No Drawings

METHOD FOR PURIFYING WASTE SOLVENT

CROSS-REFERENCE TO RELATED APPLICATIONS

This application is a National Stage Application of International Application No. PCT/KR2018/013736 filed on Nov. 12, 2018, which claims the benefit of Korean Patent Application Nos. 10-2017-0150507, filed on Nov. 13, 2017, and 10-2018-0113172, filed on Sep. 20, 2018, in the Korean Intellectual Property Office, the disclosures of which are incorporated herein in their entirety by reference.

Technical Field

The present invention relates to a method for purifying a waste solvent derived from supercritical waste liquid generated after a supercritical drying process.

BACKGROUND ART

Silica aerogel or a silica aerogel blanket is a highly porous material having high porosity and specific surface area, and low thermal conductivity, thereby being utilized as a thermal insulation material, a catalyst, a sound absorbing material, an interlayer insulation material for a semiconductor circuit, and the like in various industrial fields.

However, there is a disadvantage in that the price of a product is relatively higher than other thermal insulation materials due to expensive raw materials and production processes, and the processing cost of a large amount of waste solvent generated in the production of the product.

Among the price increase factors mentioned above, methods of reducing costs by replacing raw materials or changing production processes are difficult to apply since the methods can have a direct impact on the quality of a product.

Waste liquid generated during a drying process using a supercritical fluid is mostly composed of a solvent and water. However, since a small amount of ammonia is included therein, the waste liquid cannot be used. In order to use waste liquid, techniques of adding a solvent to dilute the waste liquid and neutralizing the same with acid are used. However, when a solvent is additionally used, there are problems in that the cost is increased and remaining ammonia is not removed at all. When waste liquid is neutralized with acid to be reused, there is a problem in that salt is generated in a final product due to the neutralization.

In addition, when carbon dioxide is used as a supercritical fluid, the carbon dioxide is dissolved in supercritical waste liquid, so that there is a problem in that ammonium carbonate salt is generated.

Accordingly, there is a need for a method for purifying a waste solvent capable of efficiently removing carbon dioxide and ammonia from a waste solvent derived from supercritical waste liquid generated after a supercritical drying process such that the waste solve is purified to high purity, and capable of minimizing the amount of solvent vaporized and lost in a purification process.

(Prior Art Document 1) CN 205145937 U (published on Apr. 13, 2016).

DISCLOSURE OF THE INVENTION

Technical Problem

An aspect of the present invention provides a method for purifying a waste solvent, the method capable of purifying a solvent to high purity by removing carbon dioxide contained in a waste solvent derived from supercritical waste liquid generated after supercritical drying by a decompression process and removing ammonia by a multi-stage distillation process, and capable of maximizing a recovery rate of solvent by minimizing solvent loss in a purification process.

Another aspect of the present invention provides a method for producing silica aerogel or a silica aerogel blanket reusing the purified solvent.

Technical Solution

According to an aspect of the present invention, there is provided a method for purifying a waste solvent, the method characterized by decompressing a waste solvent, introducing the decompressed waste solvent into a distillation column, and distilling the introduced waste solvent, wherein the distillation is performed by a multi-stage distillation method.

According to another aspect of the present invention, there is provided a method for producing silica aerogel or a silica aerogel blanket reusing the purified solvent.

Advantageous Effects

In a method for purifying a waste solvent, the method according to the present invention, carbon dioxide contained in a waste solvent derived from supercritical waste liquid generated after supercritical drying is removed in a decompression process and ammonia is removed in a multi-stage distillation process to purify the solvent to high purity. According to the present invention, a recovery rate of solvent can be maximized by minimizing solvent loss in a purification process.

Also, by controlling the operating conditions of the decompression process and the multi-stage distillation process, the purity and recovery rate of a solvent can be controlled.

Also, by reusing the purified solvent in producing silica aerogel or a silica aerogel blanket, the production cost of silica aerogel or a silica aerogel blanket can be reduced without deteriorating the physical properties thereof.

Mode for Carrying Out the Invention

Hereinafter, the present invention will be described in more detail to facilitate understanding of the present invention. In this case, it will be understood that words or terms used in the specification and claims shall not be interpreted as having the meaning defined in commonly used dictionaries. It will be further understood that the words or terms should be interpreted as having a meaning that is consistent with their meaning in the context of the relevant art and the technical idea of the invention, based on the principle that an inventor can properly define the meaning of the words or terms to best explain the invention.

The purpose of the present invention is to provide a method for purifying a waste solvent, the method capable of purifying a solvent to high purity by removing carbon dioxide contained in a waste solvent derived from supercritical waste liquid generated after supercritical drying by a decompression process and removing ammonia by a multi-stage distillation process, and capable of maximizing the recovery rate of a solvent by minimizing solvent loss in a purification process.

Specifically, the present invention includes decompressing a waste solvent, introducing the decompressed waste solvent into a distillation column, and distilling the introduced waste solvent, wherein the distillation is performed by a multi-stage distillation method.

In the present invention, the waste solvent contains a solvent, water, ammonia, and carbon dioxide, and is characterized by being derived from supercritical waste liquid generated after supercritical drying.

Also, the solvent can be specifically monohydric alcohol such as methanol, ethanol, isopropanol, and butanol; or polyhydric alcohol such as glycerol, ethylene glycol, propylene glycol, diethylene glycol, dipropylene glycol, and sorbitol, and any one thereof or a mixture of two or more thereof can be used. Among these, when considering the miscibility thereof with water and aerogel, the alcohol can be monohydric alcohol having 1 to 6 carbon atoms such as methanol, ethanol, isopropanol, and butanol, and most preferably ethanol.

Many techniques for separating a solvent or purifying a waste solvent have been so far proposed. However, such conventional techniques are intended to target a mixture of a solvent and water, and thus are different from a method for purifying a waste solvent of the present invention, the method intended to target a waste solvent derived from supercritical waste liquid including a solvent, water, a small amount of ammonia, and carbon dioxide.

When the waste solvent is reused in producing silica aerogel or a silica aerogel blanket without removing the ammonia, there can be problems in that gelation time may not be controlled due to a high pH of the waste solvent, and the physical properties of a product can be deteriorated.

Also, when carbon dioxide is used as a supercritical fluid, carbon dioxide is dissolved in the waste solvent and reacts with residual ammonia to form ammonium carbonate salt. The salt can adversely affect the thermal insulation performance of the silica aerogel or the silica aerogel blanket, and can cause fatal problems such as clogging lines of equipment during a production process.

Accordingly, in order to use the waste solvent in producing silica aerogel or a silica aerogel blanket, it is necessary to remove both ammonia and carbon dioxide.

The method for purifying a waste solvent of the present invention is characterized by first performing a decompression process for decompressing a waste solvent derived from supercritical waste liquid generated after a supercritical drying process in order to remove the carbon dioxide. When a distillation process is performed without performing the decompression process, ammonium carbonate salt can be generated in a cooling column.

In the decompression process, the temperature and pressure can be adjusted to an optimal range in order to efficiently remove carbon dioxide. Specifically, the decompression process is performed at a temperature of 30-50° C., more specifically 35-45° C., and at a pressure of 100-200 mbar, more specifically 150-200 mbar.

After the decompression process, the carbon dioxide is removed from the waste solvent, so that the pH of the waste solvent is increased compared with before the decompression process. In the present invention, the pH of the waste solvent after the decompression can be 9.0-10.0, more specifically 8.5-9.5. By removing carbon dioxide to a level satisfying the range, the formation of the ammonium carbonate salt can be minimized.

Meanwhile, the waste solvent subjected to the purification of the present invention can contain ammonia in an amount of 400-1000 ppm, more preferably 400-800 ppm. When the content of ammonia contained in a waste solve is in the above range, optimal purification efficiency can be achieved.

Also, the method of purifying a waste solvent of the present invention can maximize purification and recovery efficiency by optimizing distillation conditions.

Specifically, the method of purifying a waste solvent of the present invention is characterized by introducing the decompressed waste solvent into a distillation column and distilling the same by a multi-stage distillation n method. Specifically, the distillation of the present invention can be performed using a multi-stage distillation column involving 20-30 stages, more specifically 25-30 stages. When the number of stages is less than the above range, the effect of removing ammonia by distillation may not be complete. When greater than the above range, energy may be wasted unnecessarily with no meaningful increase in purification and recovery efficiency.

As described above, the present invention is characterized by purifying a waste solvent through multi-stage distillation in order to obtain a solvent of high purity. Since a single stage distillation method has low purification efficiency, it may not be easy to adjust such that a solvent is purified to a desired purity. Also, since the amount of solvent vaporized and lost in the distillation process is large, there can be problems in that the recovery rate of solvent, and further, the re-use ration of solvent are not high.

The distillation of the present invention can be performed at a pressure of 1-10 bar, more specifically 1-3 bar. In the method of purifying a waste solvent of the present invention, in the above ranges, high purification efficiency and a high recovery rate of solvent can be expected for energy and time spent.

When distillation is performed at a pressure lower than the above range, there may be a problem in that a separate vacuum facility may be needed. When distillation is performed at a pressure higher than the above range, there can be a problem in that the operating temperature of the distillation column increases.

The distillation of the present invention can be performed at a temperature of 70-90° C., more specifically 75-80° C. In the method of purifying a waste solvent of the present invention, in the above ranges, high purification efficiency and a high solvent recovery rate can be expected for energy and time spent.

When distillation is performed at a temperature lower than the above range, purification efficiency can be low. When distillation is performed at a temperature higher than the above range, purification efficiency can be high, but there can a problem in that a large amount of solvent is lost.

The inflow rate of the waste solvent introduced into the distillation column of the present invention can be 200-1000 kg/hr, more preferably 400-600 kg/hr. In the present invention, in the above ranges, high purification efficiency and a high recovery rate of solvent can be expected.

When the waste solvent is introduced at a rate lower than the above range, the amount of purified waste solvent is reduced so that there can be a problem in that the productivity of aerogel formation using the purified solvent is reduced. When introduced at a rate higher than the above range, there can be a problem in that purification efficiency is decreased.

In addition, the discharge rate of steam discharged from the distillation column to the inflow rate of the waste solvent introduced into the distillation column of the present invention can be 0.01-0.07, more specifically 0.015-0.07. Meanwhile, the steam can contain vapor and ammonia.

When the discharge rate of steam discharged from the distillation column to the inflow rate of the waste solvent introduced into the distillation column is less than the above range, there can be a problem in that the purification efficiency is low. When greater than the above range, the purification efficiency is high, but since a large amount of solvent is lost, there can be a problem in that the recovery rate of solvent is low.

In addition, a reboiler output based on the inflow rate of 1 kg/hr of the waste solvent introduced into the distillation column of the present invention can be 200-700 W, more specifically 320-550 W. The reboiler output refers to energy input to the distillation column. In the present invention, in the above ranges, purification efficiency and a recovery rate of solvent can be maximized.

When the reboiler output is less than the above range, there can be a problem in that the purification efficiency is low. When greater than the above range, the purification efficiency is high but since a large amount of solvent is lost, there can be a problem in that the recovery rate of solvent is low.

In addition, the reflux ratio of the present invention can be 3-10, more specifically 4-8. In general, when distillation is performed, a portion or all of steam coming out of the top of the distillation column is condensed in a condenser and becomes liquid. A portion of the liquid is refluxed back to the top, and the rest is discharged out of the distillation column. At this time, the amount of steam refluxed back to the top of the distillation column to the amount of steam discharged out of the distillation column is referred to as a reflux ratio. In the present invention, in the above ranges, purification efficiency and a recovery rate of solvent can be maximized.

When the reflux ratio is less than the above range, there can be a problem in that the purification efficiency is low. When greater than the above range, the purification efficiency is high but since a large amount of solvent is lost, there can be problems in that the recovery rate of solvent is low and energy is consumed unnecessarily.

The recovery rate of a solvent purified by the method for purifying a waste solvent of the present invention having the above-described distillation conditions can be 93% or greater, more specifically 94% or greater.

In the method of purifying a waste solvent of the present invention, ammonia is removed through multi-stage distillation, so that the recovery rate of purified solvent can be maximized by reducing the amount of solvent vaporized and lost when compared with a single stage distillation.

In addition, a solvent purified by the method of purifying a waste solvent of the present invention can be reused in production of a silica aerogel or a silica aerogel blanket.

In general, silica aerogel or a silica aerogel blanket is produced through steps of silica sol preparation-(deposition in blanket)-gelation-aging-surface modification-supercritical drying. Specifically, the purified solvent can be reused in one or more steps of silica sol preparation, aging, or surface modification.

Meanwhile, a solvent purified by the method of purifying a waste solvent of the present invention can contain ammonia in an amount of 50 ppm or less, specifically 30 ppm or less, and more specifically 20 ppm or less.

A solvent containing ammonia within the above range can be reused in a production process of silica aerogel or a silica aerogel blanket and implement products having the same or similar level of physical properties without deteriorating the physical properties thereof. Thereby, the amount of solvent to be used is reduced, so that the production cost of silica aerogel or a silica aerogel blanket and the processing cost of waste liquid can be effectively reduced.

Hereinafter, examples of the present invention will be described in detail so that those skilled in the art can easily carry out the present invention. The present invention can, however, be embodied in many different forms and is not limited to the examples set forth herein.

EXAMPLE 1

A mixed solution prepared by mixing tetraethyl orthosilicate (TEOS) and ethanol at a weight ratio of 3:1 was added with a solution of hydrochloric acid diluted with water (concentration=0.15 wt %) such that the pH of the mixed solution was 1 and then mixed to prepare silica sol (silica content in silica sol=4 wt %). Next, the silica sol was added with an ammonia catalyst at a volume ratio of 100:0.5 (silica sol:ammonia catalyst), deposited in glass fiber, and gelled to prepare a silica wet gel composite.

Thereafter, the silica wet gel composite was immersed in ethanol, and then aged for 2 hours in an oven of 70° C. The aged silica wet gel composite was surface modified for 5 hours at 70° C. using a surface modification solution which is a mixture of ethanol and HMDS (volume ratio of ethanol: HMDS: 1:19).

Subsequently, the surface-modified silica wet gel composite was placed in an extractor in supercritical equipment to perform supercritical drying thereon using supercritical $CO_2$, and was dried at 150° C. and atmospheric pressure for 1 hour to produce a silica aerogel blanket.

After performing decompression at 40° C. and 170 mbar on waste ethanol derived from supercritical waste liquid generated after the supercritical drying, the waste ethanol was purified by performing multi-stage distillation under conditions that the reboiler output is 374 W and the reflux ratio is 4 based on the inflow rate of 1 kg/hr of the waste ethanol introduced into the distillation column.

EXAMPLE 2

Waste ethanol was purified in the same manner as in Example 1 except that the distillation was performed under the conditions set forth in Table 1.

Comparative Examples 1 to 4

Waste ethanol was purified in the same manner as in Example 1 except that the decompression process was not performed and the distillation was performed under the specific conditions set forth in Table 1.

Comparative Example 5

Waste ethanol was purified in the same manner as in Example 1 except that the decompression process was not performed, a single stage distillation process was performed instead of the multi-stage distillation process, and the distillation was performed under the specific conditions set forth in Table 1.

Experimental Example

Whether or not the decompression process was performed, the pH of the waste ethanol introduced into the distillation column, the concentration of residual ammonia after the distillation process, the rate of ethanol recovery, and the generation of salt in a cooling column were measured and the results are shown in Table 1.

TABLE 1

| | Example 1 | Example 2 | Comparative Example 1 | Comparative Example 2 | Comparative Example 3 | Comparative Example 4 | Comparative Example 5 |
|---|---|---|---|---|---|---|---|
| Number of distillation stages (stage) | 25 | 25 | 25 | 25 | 25 | 25 | 1 |
| Whether or not decompression process was performed | ○ | ○ | X | X | X | X | X |
| pH of waste ethanol introduced into distillation column | 9.5 | 9.5 | 8.2 | 8.2 | 8.2 | 8.2 | 8.2 |
| Concentration (ppm) of ammonia contained in waste ethanol | 420 | 420 | 420 | 420 | 420 | 420 | 420 |
| Reboiler output (A) | 2.0 | 2.3 | 1.7 | 2.0 | 2.0 | 2.3 | — |
| Reflux ratio | 4 | 4 | 4 | 4 | 8 | 5 | — |
| Discharge rate of steam based on inflow rate of waste ethanol | 0.032 | 0.051 | 0.02 | 0.03 | 0.017 | 0.069 | 0.076 |
| Concentration (ppm) of residual ammonia | <20 | <20 | <20 | <20 | <20 | <20 | 108 |
| Recovery rate (%) of ethanol | 96.8 | 94.9 | 98 | 97 | 98.3 | 93.1 | 92.4 |
| Generation of salt in cooling column | No | No | Yes | Yes | Yes | Yes | Yes |

As shown in Table 1, in Examples 1 and 2 of the present invention, the decompression process is performed to remove carbon dioxide in advance before the distillation, so that the pH of the waste ethanol introduced into the distillation column is high when compared with Comparative Examples in which the distillation is performed without performing the decompression process, and salt is not generated in the cooling column during the distillation process. Thereafter, the multi-state distillation process was performed to recover ethanol of high purity having a concentration of residual ammonia of less 20 ppm, and the recovery rate of the ethanol was 93% or greater, which confirms that ethanol loss in the distillation process was minimized.

However, in Comparative Examples 1 to 4, although ethanol of high purity having a concentration of residual ammonia of less 20 ppm was obtained at a recovery rate of 93% or greater, the decompression process was not performed before the distillation process, so that salt was generated in the cooling column during the distillation process.

Meanwhile, in Comparative Example 5, the waste ethanol was purified through single stage distillation, so that the recovered ethanol had a concentration of residual ammonia greater than 100 ppm, which is not suitable to be reused for producing silica aerogel or a silica aerogel blanket, and purification efficiency was not good since the recovery rate of the ethanol was not high. Also, since the decompression process was not performed, salt was generated in the cooling column during the distillation process.

The foregoing description of the present invention has been presented for purposes of illustration. It will be understood by those skilled in the art that various changes in form and details can be made therein without departing from the spirit and scope of the invention. It is therefore to be understood that the above-described embodiments are illustrative in all aspects and not restrictive.

The invention claimed is:

1. A method for purifying a waste solvent, the method comprising:
    decompressing a waste solvent containing ammonia and carbon dioxide, wherein the decompressing is performed at a temperature of 30-50° C. and a pressure of 100-200 mbar to remove carbon dioxide;
    introducing the decompressed waste solvent into a distillation column; and
    distilling the introduced decompressed waste solvent to yield a purified waste solvent, wherein the distillation is performed by a multi-stage distillation method.

2. The method of claim 1, wherein an amount of ammonia contained in the decompressed waste solvent introduced into the distillation column is 400-1000 ppm, and an amount of ammonia contained in the purified waste solvent is 50 ppm or less.

3. The method of claim 1, wherein an amount of ammonia contained in the purified waste solvent is 30 ppm or less.

4. The method of claim 1, wherein the waste solvent is derived from supercritical waste liquid generated after a supercritical drying process.

5. The method of claim 1, wherein a pH of the waste solvent after the decompression is 9.0-10.0.

6. The method of claim 1, wherein the distillation is performed by a multi-stage distillation method involving 20-30 stages.

7. The method of claim 1, wherein a ratio of a discharge rate by weight of steam discharged from the distillation column with respect to an inflow rate by weight of the waste solvent introduced into the distillation column is 0.01-0.07.

8. The method of claim 1, wherein a reboiler output based on the inflow rate of 1 kg/hr of the waste solvent introduced into the distillation column is 200-700 W.

9. The method of claim 1, wherein the distilling has a reflux ratio of 3-10.

10. The method of claim 1, wherein a recovery rate of the purified solvent is 93% or greater.

11. The method of claim 1, wherein no salt is formed in a cooling column during the distilling.

* * * * *